US009675238B2

(12) United States Patent
Iida et al.

(10) Patent No.: US 9,675,238 B2
(45) Date of Patent: Jun. 13, 2017

(54) ENDOSCOPIC DEVICE

(71) Applicant: FUJIFILM Corporation, Tokyo (JP)

(72) Inventors: Takayuki Iida, Kanagawa (JP);
Toshihiko Kaku, Kanagawa (JP);
Hiroshi Yamaguchi, Kanagawa (JP);
Takaaki Saito, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 11 days.

(21) Appl. No.: 14/686,687

(22) Filed: Apr. 14, 2015

(65) Prior Publication Data

US 2015/0216400 A1    Aug. 6, 2015

Related U.S. Application Data

(62) Division of application No. 13/562,149, filed on Jul. 30, 2012, now abandoned.

(30) Foreign Application Priority Data

Aug. 10, 2011    (JP) ................................. 2011-174818

(51) Int. Cl.
*A61B 1/04*    (2006.01)
*A61B 1/06*    (2006.01)
(Continued)

(52) U.S. Cl.
CPC ........ *A61B 1/0638* (2013.01); *A61B 1/00006* (2013.01); *A61B 1/00009* (2013.01);
(Continued)

(58) Field of Classification Search
CPC . A61B 1/0638; A61B 1/0061; A61B 1/00006; A61B 1/00045; A61B 1/0653; A61B 1/0661; A61B 5/489
(Continued)

(56) References Cited

U.S. PATENT DOCUMENTS 4,706,657 A * 11/1987 Miyagi ................ A61B 1/0669
600/178
4,746,974 A    5/1988 Matsuo
(Continued)

FOREIGN PATENT DOCUMENTS

EP    1 488 732 A1    12/2004
EP    1795798 A1    6/2007
(Continued)

OTHER PUBLICATIONS

Japanese Decision of Refusal dated Sep. 16, 2014 with an English translation thereof.
(Continued)

*Primary Examiner* — Anhtuan T Nguyen
*Assistant Examiner* — Jae Woo
(74) *Attorney, Agent, or Firm* — McGinn IP Law Group, PLLC.

(57) ABSTRACT

An endoscopic device that irradiates a plurality of illuminating lights having different spectrums from each other onto a subject at a front edge of an endoscope inserting module and captures the subject to obtain an observation image, includes an illuminating module that generates the plurality of illuminating lights, an imaging module that captures the subject and outputs an image signal of the observation image, a light intensity ratio control module that controls the illuminating module to irradiate the plurality of illuminating lights onto the subject with a set light intensity ratio by setting the light intensity ratio of the plurality of illuminating lights for every observation image, and a color tone correcting module that corrects the color tone of the image signal so as to obtain the observation image with substantially a same color tone even though the light intensity ratio is changed.

16 Claims, 8 Drawing Sheets

(51) Int. Cl.
    *A61B 1/00*                 (2006.01)
    *A61B 5/00*                 (2006.01)

(52) U.S. Cl.
    CPC ............ *A61B 1/00045* (2013.01); *A61B 1/04* (2013.01); *A61B 1/0653* (2013.01); *A61B 1/0661* (2013.01); *A61B 5/489* (2013.01); *A61B 5/7257* (2013.01); *A61B 1/063* (2013.01)

(58) Field of Classification Search
    USPC ........................................ 600/160, 178, 180
    See application file for complete search history.

(56) References Cited

U.S. PATENT DOCUMENTS

| | | | |
|---|---|---|---|
| 4,951,134 A * | 8/1990 | Nakasima | H04N 17/02 348/223.1 |
| 5,029,016 A | 7/1991 | Hiyama et al. | |
| 5,282,030 A * | 1/1994 | Nishimura | A61B 1/05 348/242 |
| 5,749,830 A | 5/1998 | Kaneko et al. | |
| 5,864,361 A * | 1/1999 | Sekiya | A61B 1/045 348/65 |
| 5,894,322 A | 4/1999 | Hamano et al. | |
| 6,577,073 B2 | 6/2003 | Shimizu et al. | |
| 6,712,756 B1 * | 3/2004 | Kura | A61B 1/00059 600/117 |
| 6,749,562 B2 | 6/2004 | Nakamura et al. | |
| 7,005,679 B2 | 2/2006 | Tarsa et al. | |
| 7,658,710 B2 * | 2/2010 | Ueno | A61B 1/00009 348/68 |
| 7,704,206 B2 * | 4/2010 | Suzuki | A61B 1/043 348/70 |
| 7,791,092 B2 | 9/2010 | Tarsa et al. | |
| 7,857,751 B2 | 12/2010 | Iketani et al. | |
| 7,969,097 B2 | 6/2011 | Van De Ven et al. | |
| 8,038,317 B2 | 10/2011 | Van De Ven et al. | |
| 8,169,470 B2 * | 5/2012 | Ishihara | A61B 1/00009 348/68 |
| 8,193,735 B2 | 6/2012 | Wei et al. | |
| 8,231,526 B2 * | 7/2012 | Yabe | A61B 1/00009 600/160 |
| 2002/0016533 A1 * | 2/2002 | Marchitto | A61B 5/0066 600/310 |
| 2002/0070681 A1 | 6/2002 | Shimizu et al. | |
| 2003/0176768 A1 | 9/2003 | Gono et al. | |
| 2004/0026683 A1 * | 2/2004 | Yamada | H01L 25/0753 257/10 |
| 2004/0263500 A1 * | 12/2004 | Sakata | H04N 9/3105 345/204 |
| 2005/0010081 A1 | 1/2005 | Doguchi et al. | |
| 2005/0194876 A1 | 9/2005 | Shimada et al. | |
| 2006/0022214 A1 | 2/2006 | Morgan et al. | |
| 2006/0152926 A1 | 7/2006 | Hama et al. | |
| 2006/0178565 A1 | 8/2006 | Matsui et al. | |
| 2006/0256191 A1 | 11/2006 | Iketani et al. | |
| 2007/0171375 A1 * | 7/2007 | Mizuuchi | H04N 9/3129 353/30 |
| 2007/0282169 A1 | 12/2007 | Tsujita | |
| 2008/0017787 A1 | 1/2008 | Okawa et al. | |
| 2008/0205477 A1 | 8/2008 | Hama et al. | |
| 2008/0208006 A1 | 8/2008 | Farr | |
| 2008/0262316 A1 | 10/2008 | Ajima et al. | |
| 2008/0281154 A1 | 11/2008 | Gono et al. | |
| 2008/0283770 A1 | 11/2008 | Takahashi | |
| 2008/0294105 A1 | 11/2008 | Gono et al. | |
| 2009/0024000 A1 * | 1/2009 | Chen | A61B 1/00165 600/180 |
| 2009/0036743 A1 | 2/2009 | Yabe et al. | |
| 2009/0040598 A1 | 2/2009 | Ito | |
| 2009/0058999 A1 | 3/2009 | Gono et al. | |
| 2009/0062617 A1 | 3/2009 | Mizuyoshi | |
| 2009/0167149 A1 | 7/2009 | Ito | |
| 2009/0203966 A1 | 8/2009 | Mizuyoshi | |
| 2009/0256905 A1 * | 10/2009 | Tashiro | H04N 5/2256 348/65 |
| 2009/0306478 A1 | 12/2009 | Mizuyoshi | |
| 2010/0119110 A1 | 5/2010 | Kanda | |
| 2010/0141747 A1 | 6/2010 | Kubo et al. | |
| 2010/0168584 A1 | 7/2010 | Fujinuma et al. | |
| 2010/0280322 A1 | 11/2010 | Mizuyoshi | |
| 2011/0034770 A1 * | 2/2011 | Endo | A61B 1/0638 600/118 |
| 2011/0077465 A1 * | 3/2011 | Mizuyoshi | A61B 1/00096 600/180 |
| 2011/0237895 A1 * | 9/2011 | Yoshida | A61B 1/00009 600/180 |
| 2012/0116159 A1 * | 5/2012 | Mizuyoshi | A61B 1/0653 600/109 |

FOREIGN PATENT DOCUMENTS

| | | |
|---|---|---|
| EP | 2 020 202 A2 | 2/2009 |
| EP | 2 130 484 A1 | 12/2009 |
| EP | 2 301 413 A1 | 3/2011 |
| EP | 2 301 418 A1 | 3/2011 |
| JP | S62-183293 A | 8/1987 |
| JP | 63-155984 A | 6/1988 |
| JP | H 4-314181 A | 11/1992 |
| JP | 6040174 B | 5/1994 |
| JP | 2001-137172 A | 5/2001 |
| JP | 2002-95635 A | 4/2002 |
| JP | 3583731 | 8/2004 |
| JP | 3583731 B2 | 11/2004 |
| JP | 2005-6856 A | 1/2005 |
| JP | 2005-122237 A | 5/2005 |
| JP | 2005-124823 A | 5/2005 |
| JP | 2005-198794 A | 7/2005 |
| JP | 2005-279255 A | 10/2005 |
| JP | 2006-2115 | 1/2006 |
| JP | 2006-006968 A | 1/2006 |
| JP | 2006-122335 A | 5/2006 |
| JP | 2006-173324 A | 6/2006 |
| JP | 2006-212335 A | 8/2006 |
| JP | 2006-341077 A | 12/2006 |
| JP | 2007-139822 A | 6/2007 |
| JP | 2007-252809 A | 10/2007 |
| JP | 2008-284030 A | 11/2008 |
| JP | 2009-25401 A | 2/2009 |
| JP | 2009-34224 A | 2/2009 |
| JP | 2009-056248 A | 3/2009 |
| JP | 2009-153621 A | 7/2009 |
| JP | 2009-153712 A | 7/2009 |
| JP | 2010-035922 A | 2/2010 |
| JP | 2010-113616 A | 5/2010 |
| JP | 2010-136748 A | 6/2010 |
| JP | 2011-010998 A | 1/2011 |
| JP | 2011010998 A * | 1/2011 |
| JP | 2011-36361 A | 2/2011 |
| WO | WO 02/12127 A2 | 2/2002 |
| WO | WO 2005/104926 A1 | 11/2005 |
| WO | WO 2008/048688 A2 | 4/2008 |
| WO | WO 2011/004801 A1 | 1/2011 |

OTHER PUBLICATIONS

United States Office Action dated Mar. 13, 2015 in co-pending U.S. Appl. No. 12/853,903.
Decision of Rejection dated Nov. 12, 2013 with an English translation.
Chinese First Office Action dated Nov. 13, 2013, with English translation.
United States Office Action dated Jul. 15, 2014 in U.S. Appl. No. 12/853,903.
European Office Action dated May 21, 2014.
JP-OA 2009-159962 Pretrial Reexamination Report prepared by JPO on Mar. 14, 2014.
Japanese Office Action dated Jun. 4, 2013 with a partial English translation thereof.

(56) References Cited

OTHER PUBLICATIONS

European Search Report dated Dec. 6, 2012.
Japanese Office Action dated Apr. 22, 2014 with a partial English translation.
Chinese First Office Action dated Nov. 13, 2013 with an English translation.
United State Office Action dated Jul. 10, 2013 in U.S. Appl. No. 12/853,903.
United States Office Action dated Dec. 13, 2013 in U.S. Appl. No. 13/382,282.
United States Office Action dated Aug. 12, 2014 in U.S. Appl. No. 13/562,149.
United States Office Action dated Jan. 14, 2015 in U.S. Appl. No. 13/562,149.
International Search Report in PCT/JP2010/061432 dated Sep. 28, 2010 (English Translation Thereof).
Japanese Office Action dated Nov. 6, 2012, with English translation.
Extended European Search Report dated Jan. 24, 2013.
Japanese Office Action dated Feb. 5, 2013, with English translation.
European Search Report dated dated Nov. 22, 2010.
United States Office Action dated Dec. 13, 2012, in U.S. Appl. No. 12/853,903.
Japanese Office Action dated Jun. 18, 2013, with English translation.
European Office Action dated May 4, 2015.

\* cited by examiner

ENDOSCOPIC DEVICE

CROSS-REFERENCE TO RELATED APPLICATIONS

The present application is a Divisional application of U.S. patent application Ser. No. 13/562,149, filed on Jul. 30, 2012, which is based on and claims priority from Japanese Patent Application No. 2011-174818 filed on Aug. 10, 2011, the entire contents of which are hereby incorporated by reference.

BACKGROUND

1. Technical Field

The present invention relates to an endoscopic device.

2. Related Art

An endoscopic device that is used in the medical field performs a normal observation that observes a subject image almost same as the observation by naked eyes by irradiating white light onto a subject in a biological body as well as a narrow band observation that observes a subject image by irradiating narrow band light having narrower wavelength band than the light irradiated during the normal observation. The narrow band observation observes the blood capillary or a micro pattern of a superficial portion of the mucous membrane in the biological body with a good contrast and helps for an early detection of lesions.

The endoscopic device that is available for the narrow band observation preferably changes the light intensities of the light emitted from the white light and the narrow band light depending on the observation scene. For example, the endoscopic device available for the narrow band observation increases the light intensity of the narrow band light in order to easily observe the blood capillary of the superficial portion of the mucous membrane at the time of near view imaging and increases the light intensity of the white light at the time of distant view imaging to resolve the insufficient amount of irradiated light. By doing this, an observation image suitable for endoscopic diagnosis may be obtained. An endoscopic device that performs the above-mentioned narrow band observation is disclosed in JP-A-2011-10998.

However, when the white light and the narrow band light are irradiated onto the subject while appropriately changing the emitted light intensity ratio of the white light and the narrow band light, the color shade of the illuminating light is changed. As a result, the color tone of the observation image is changed. If the color tone of the observation image is changed, an operator may be bothered by a feeling of strangeness, which may influence an accurate endoscopic diagnosis. Further, if a predetermined image processing is performed to the observation image, an intended image may not be obtained.

In the present invention, an endoscopic device can correct the observation image so that the color tone of the observation image is not changed even though the light intensity ratio of the illuminating light is changed when each illuminating light is emitted from a plurality of light sources that emit light having different spectrums, thereby performing accurate endoscopic diagnosis by observing using illuminating light with an optimal light intensity ratio.

SUMMARY OF INVENTION

According to an aspect of the invention, an endoscopic device that irradiates a plurality of illuminating light having different spectrums from each other onto a subject at a front edge of an endoscope inserting module and captures the subject to obtain an observation image. The endoscopic device includes an illuminating module, an imaging module, a light intensity ratio control module, and a color tone correcting module. The illuminating module generates the plurality of illuminating light. The imaging module captures the subject and output an image signal of the observation image. The light intensity ratio control module controls the illuminating module to irradiate the plurality of illuminating light onto the subject with a set light intensity ratio by setting the light intensity ratio of the plurality of illuminating light for every observation image. The color tone correcting module corrects the color tone of the image signal so as to obtain the observation image with substantially the same color tone even though the light intensity ratio is changed.

When the illuminating light is emitted from a plurality of light sources that emit light having different spectrums, the endoscopic device according to the present invention may correct the observation image such that the color tone of the observation image is not changed even though the light intensity ratio of the illuminating light is changed. Therefore, the observation is performed with the illuminating light at an optimal light intensity ratio, so that it is possible to easily diagnose an object to be observed and accurately perform diagnosis using the endoscope.

DETAILED DESCRIPTION

Hereinafter, exemplary embodiments of the present invention will be described with reference to the accompanying drawings.

Figure 1:
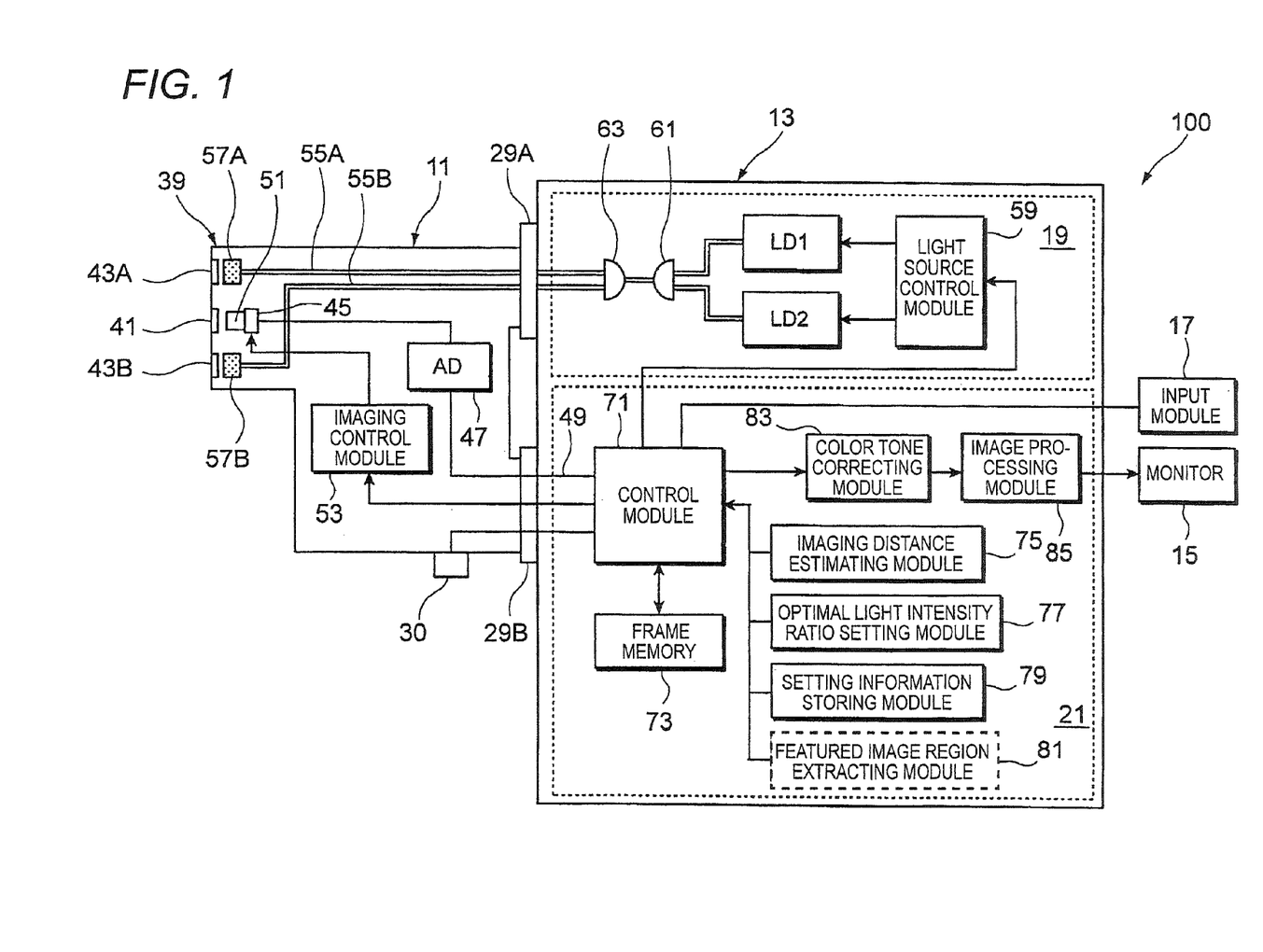
FIG. 1 is a block diagram of an endoscopic device according to an exemplary embodiment of the present invention.
Figure 2:
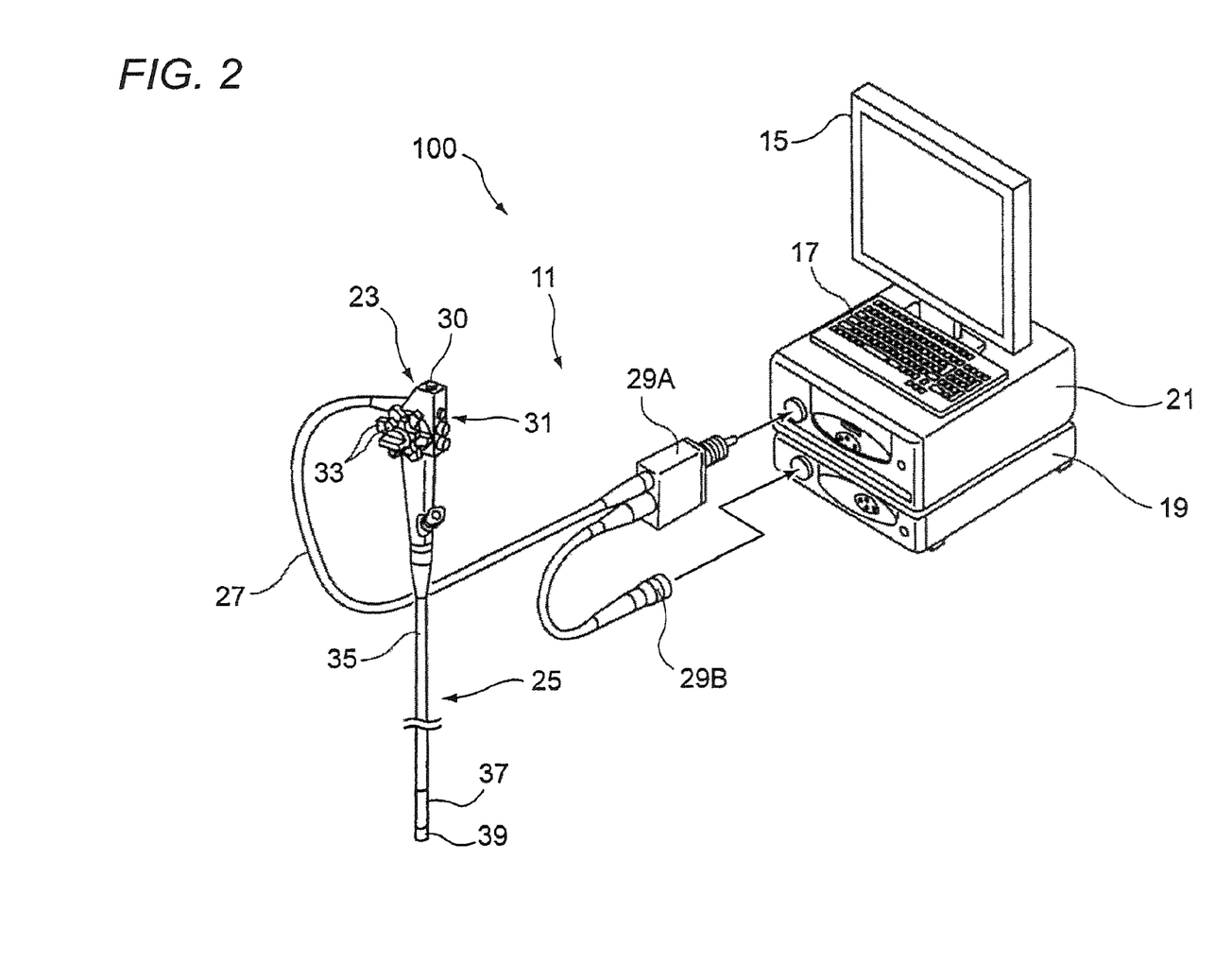
FIG. 2 is an external view illustrating a specific configuration example of the endoscopic device.

FIG. 1 is a block diagram of the configuration of an endoscopic device according to an exemplary embodiment of the present invention, and FIG. 2 is an external view illustrating a specific configuration example of the endoscopic device.

An endoscopic device 100, as shown in FIG. 1, includes an endoscope 11, a control device 13, a monitor 15, and an input module 17 such as a keyboard or a mouse that inputs information to the control device 13. The control device 13 is constituted by a light source device 19 that outputs illuminating light and a processor 21 that performs signal processing of an observation image.

The endoscope 11, as shown in FIG. 2, includes a main body operating module 23, an inserting module 25 that is coupled to the main body operating module 23 to be inserted into the subject (body cavity), and a universal cord 27 that is connected to the main body operating module 23. The front edge of the universal cord 27 is provided with a light guide (LG) connector 29B that is connected to the light source device 19 and a video connector 29A that is connected to the processor 21.

Various operating buttons 31 including a button for suctioning, air supplying, and water supplying at the front edge side of the inserting module 25, a shutter button at the time of imaging, a mode switching button that switches an observation mode, and a confirmation button 30 for confirming a lesion area at the time of endoscopic diagnosis, which will be described below, are provided together in the main body operating module 23 of the endoscope 11. A pair of angle knobs 33 is provided in the main body operating module 23.

The inserting module 25 is constituted by a flexible part 35, a curvature part 37, and a front edge part (an endoscope front edge part) 39 in order from the main body operating module 23 side. The curvature part 37 is remotely curved by rotating the angle knob 33 of the main body operating module 23, which allows the front edge part 39 to be oriented in a desired direction.

At the front edge part 39 of the endoscope, as shown in FIG. 1, an observation window 41 of an imaging optical system and illumination windows 43A, 43B of an illuminating optical system are arranged. Each of the illumination windows 43A, 43B emits illuminating light onto the subject. The reflected light from the subject is detected (captured) by an image pickup device 45 through the observation window 41. An image signal output from the image pickup device 45 is digitalized by an analogue/digital (A/D) converting module 47 and then, the image signal is input to the processor 21 through a signal cable 49 to be subjected to an appropriate image processing thereon, and the image signal is displayed on the monitor 15 connected to the processor 21.

The imaging optical system includes the image pickup device 45 such as a charge coupled device (CCD) type image sensor or a complementary metal oxide semiconductor (CMOS) type image sensor and an optical member 51 such as a lens that forms the observation image onto the image pickup device 45. The image pickup device 45 may include a color filter of complementary color such as CMY or CMYG in addition to a color filter of RGB primary color. An imaging condition of the image pickup device 45 such as a shutter speed or an iris diaphragm is set by an imaging control module 53.

The illuminating optical system includes the light source device 19, a pair of optical fibers 55A, 55B connected to the light source device 19 through the light guide connector 29B, and wavelength converting members 57A, 57B which are disposed at light emitting ends of the optical fibers 55A, 55B, respectively. The light source device 19 includes laser light sources LD1, LD2 which are semiconductor light emitting elements, a light source control module 59 that controls to drive the laser light sources LD1, LD2, a combiner 61 that combines the light emitted from the laser light sources LD1, LD2, and a coupler 63 that divides the light emitted from the combiner 61 into the optical fibers 55A, 55B.

The laser light source LD1 is a blue light emitting semiconductor laser having a central wavelength of 445 nm and combines the blue laser light and fluorescence obtained by exciting the wavelength converting members 57A, 57B to generate white illuminating light. The laser light source LD2 is a violet light emitting semiconductor laser having a central wavelength of 405 nm. For example, a broad area type InGaN-based laser diode may be used as the laser light sources. If the central wavelength of the emitted light is in a range between 370 nm and 470 nm, the laser light source LD2 allows good narrow band observation in which the blood capillary or a micro pattern of a superficial portion of the mucous membrane is emphasized.

A band width of wavelength of each of the laser light sources LD1 and LD2 at half maximum is equal to or less than 60 nm, preferably equal to or less than 40 nm, more preferably equal to or less than 20 nm. In view of the light intensity, the band width at half maximum is preferably equal to or less than 10 nm.

The light source control module 59 controls the light intensity of each of the laser light sources LD1, LD2 based on the command of the control module 71 of the processor 21. The emitted light passes through the optical fibers 55A, 55B to be guided to the endoscope front edge part 39 and then is irradiated on the wavelength converting members 57A, 57B. As described above, the light source control module 59 controls the light emitted from the laser light sources LD1, LD2 so as to simultaneously emit light from the illumination windows 43A, 43B with an arbitrary light intensity at an arbitrary timing.

Figure 3:
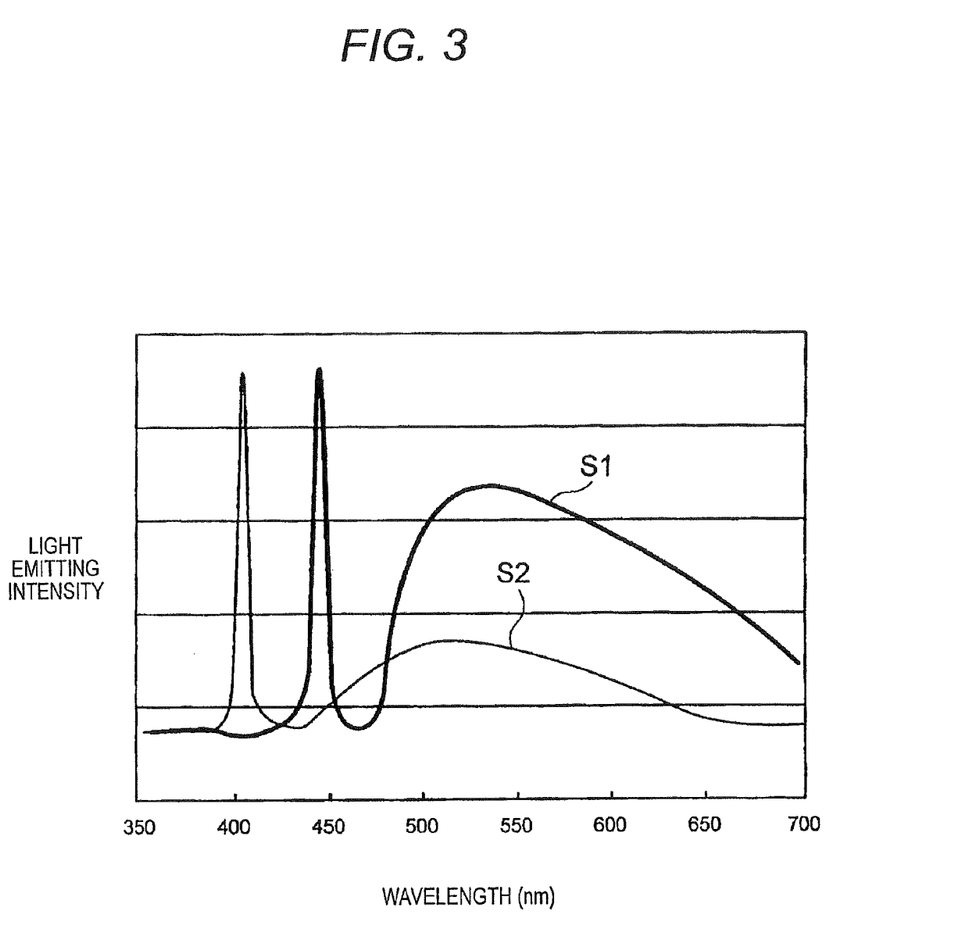
FIG. 3 is a graph illustrating spectral characteristics of emitted light.

The wavelength converting members 57A, 57B are configured to include a plurality kinds of fluorescent substances (for example, YAG fluorescence or fluorescence including, for example, BAM (BaMgAl.sub.10O.sub.37)) that absorb a part of a blue laser light emitted from the laser light source LD1 and emits green to yellow color light. By the wavelength converting members 57A, 57B, as the spectral characteristics of the emitted light is shown in FIG. 3, the blue laser light of the laser light source LD1 and the green to yellow excited light obtained by the wavelength conversion of the blue laser light are composited to generate white light having high color rendering property that is represented by a profile S1.

With respect to the light emitted from the laser light source LD2, the absorption of the fluorescence is low and the wavelength converting efficiency by the wavelength converting members 57A, 57B is low. Therefore, the intensity of the fluorescence generated by the laser light source LD2 is insufficient as compared with the laser light source LD1. As shown in a profile S2 of FIG. 3, the light emitted from the laser light source LD2 is mostly narrow band light having a central wavelength of 405 nm, which is substantially shorter than the white light, and having a narrower wavelength band than the white light.

With the above-mentioned configuration, the laser light emitted from the laser light sources LD1, LD2 are guided to the endoscope front edge part 39 by the optical fibers 55A, 55B so that the white light and violet narrow band light are emitted from both illumination windows 43A, 43B of the endoscope front edge part 39 with an arbitrary light intensity ratio based on the command from the control module 71. As described above, the laser light from both laser light sources LD1, LD2 is irradiated onto the subject through the same fluorescent substance at the illumination windows 43A, 43B, so that the laser light is irradiated onto the subject so as to be substantially equally spread from the same portion. Therefore, there is no difference in the illumination range by the emitted light or difference in the intensity distribution, which allows obtaining a good observation image.

Specifically, the control module 71 outputs a control signal to the light source control module 59 and the light source control module 59 outputs a driving signal, which turns ON/OFF the laser light sources LD1, LD2 by the input control signal.

The laser light sources LD1, LD2 emit light with a light intensity based on the input driving signal. Therefore, the intensity or light intensity ratio (color shade) of the light emitted from the illumination windows 43A, 43B is adjusted. Accordingly, the control module 71 functions as a light intensity control module that changes the light intensity ratio of the white light and the narrow band light of the illuminating light.

The processor 21 includes the control module 71, a frame memory 73 that stores the picked up image signal, an imaging distance estimating module 75 that estimates an imaging distance to the subject based on the brightness information of the image signal, an optimal light intensity ratio setting module 77 that sets the light intensity ratio suitable for observation, and a setting information storing module 79 that stores various information for setting the optimal light intensity ratio. The processor 21 further includes a color tone correcting module 83 that corrects the color tone of the image signal and an image processing module 85.

With the above configuration of the control device 13, the control module 71 sets the light intensity ratio of the light emitted from the laser light sources LD1, LD2 which is optimal for the observation image with respect to the image signal of the observation image including, for example, the lesion area. Therefore, the observation image may be always suitable for the endoscopic diagnosis.

Hereinafter, the setting of the light intensity ratio will be described with a specific observation procedure.

Figure 4:
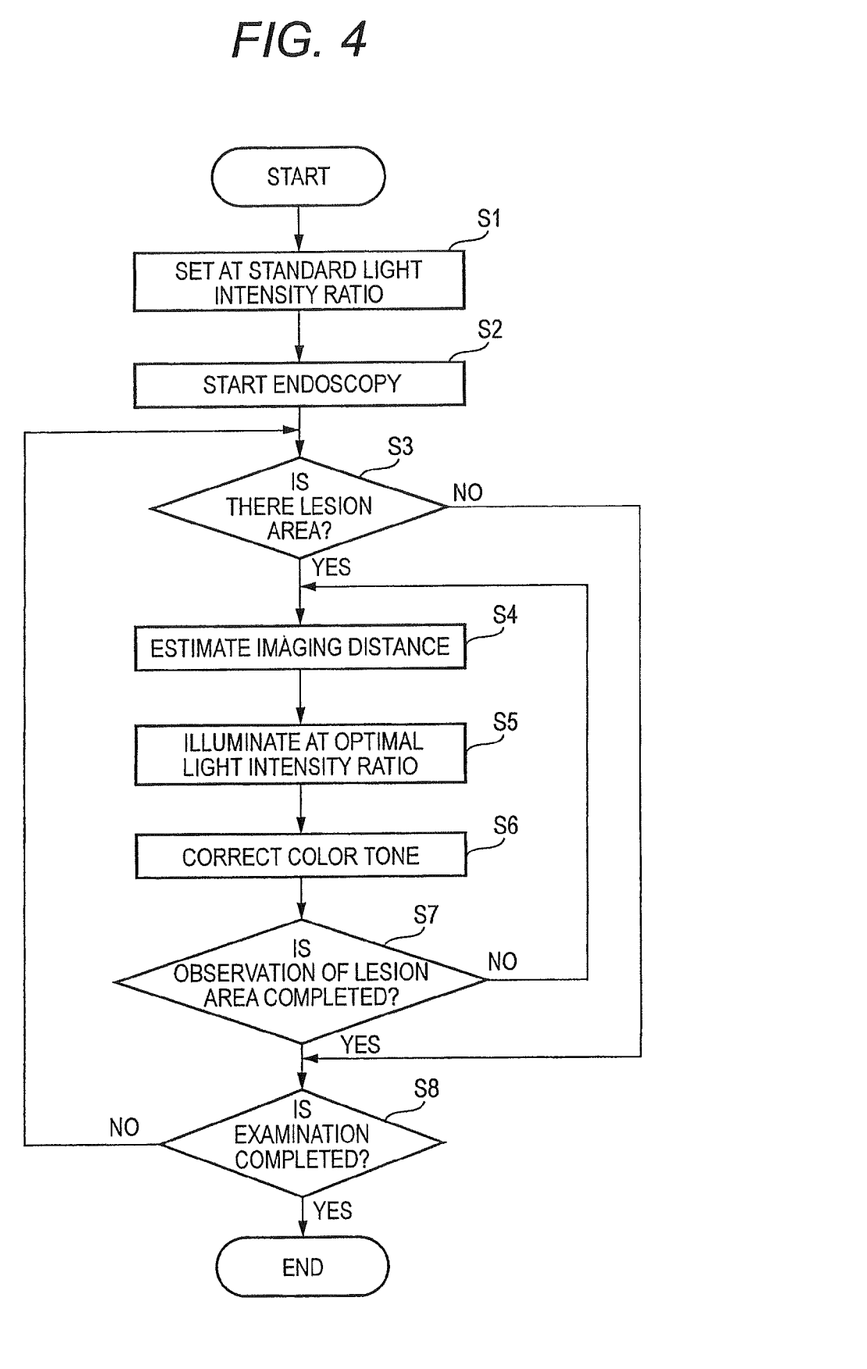
FIG. 4 is a flowchart of observational procedures in a body cavity by the endoscopic device.

FIG. 4 illustrates a flowchart of an observation procedure in a body cavity by the endoscopic device 100. In the observation procedure illustrated as an example, the operator of the endoscopic device 100 sets the light intensity ratio of the light emitted from the laser light sources LD1, LD2 to a standard light intensity ratio for endoscopy (S1). The light intensity ratio may be manually or automatically set, for example, input from the input module 17 connected to the control device 13 or set by referring to the standard light intensity ratio stored in the setting information storing module 79 in advance.

The standard light intensity ratio is a ratio when the laser light source LD2 is turned OFF and only the laser light source LD1 (445 nm) is turned ON, that is, LD1 ($\lambda_{445}$):LD2 ($\lambda_{405}$)=100:0, which becomes illuminating light for normal observation by the white light.

The operator starts the endoscopy by inserting the endoscope inserting module 25 to which the white light from the front edge is emitted into the subject (S2). The control module 71 outputs the observation image of the inside of the subject to the monitor 15 so as to display the observation image on the monitor 15. The operator identifies the lesion area from the displayed observation image. If there is a lesion area (S3), the operator presses the confirmation button 30 (see, for example, FIGS. 1 and 2) of the main body operating module 23.

Figure 5:
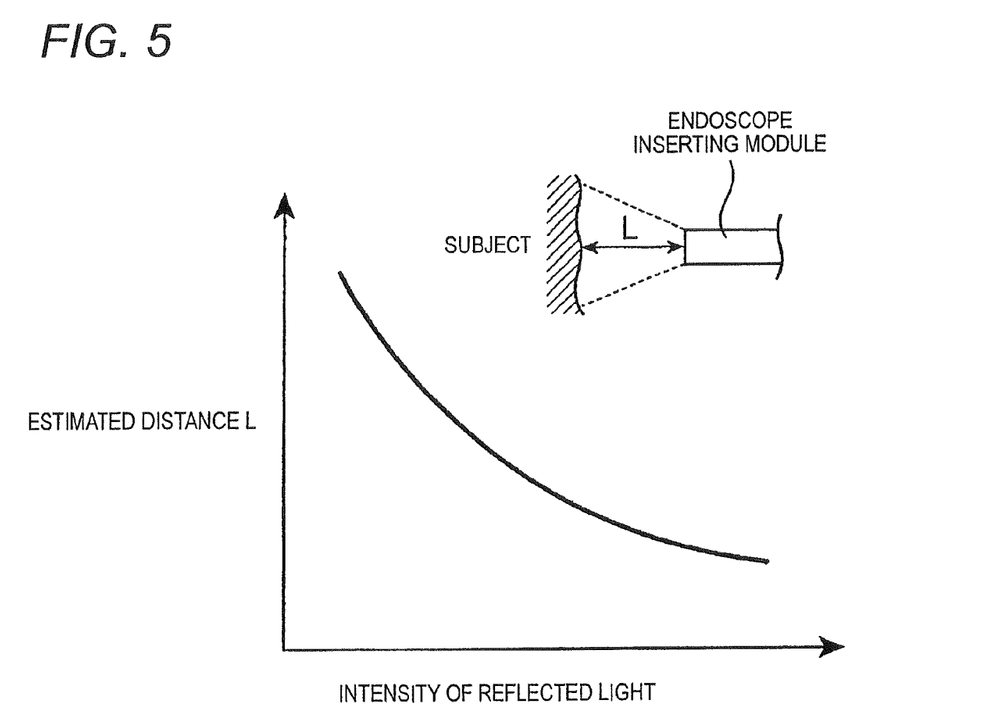
FIG. 5 is a graph illustrating distance table information representing the relationship between a reflected light intensity and an estimated distance L.

The control module 71 receives a signal that the confutation button 30 is pressed and estimates the imaging distance to the subject based on the information of AE value which is an imaging condition of the observation image and the information of the illuminating light intensity that is set by the light source control module 59 (S4). The AE value and the distance table information, which indicates the relationship between the estimated distance L and the reflection light intensity defined by the illuminating light intensity, are prepared in advance as shown in FIG. 5, and then the imaging distance is estimated by referring to the distance table information. The distance table information is prepared for every AE value (for example, shutter speed, iris diaphragm, and brightness) at the time of imaging and imaging condition of the illuminating light intensity, and the distance table information is stored in the setting information storing module 79. The control module 71 selectively refers to the distance table information corresponding to the imaging condition of the observation image to estimate the imaging distance L.

Figure 6:
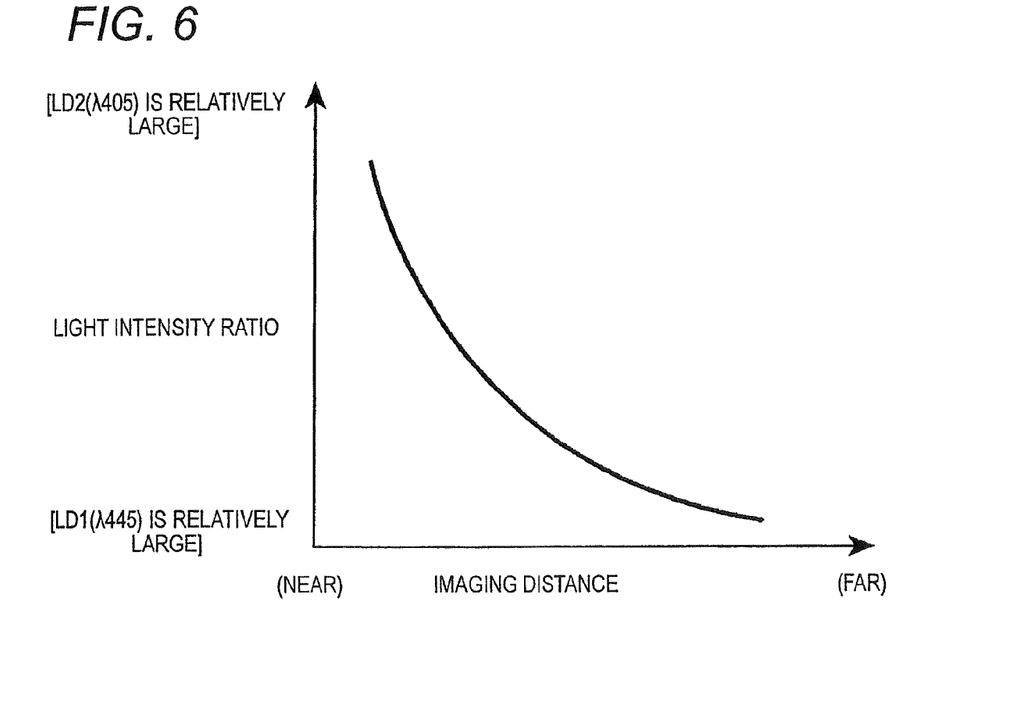
FIG. 6 is a graph illustrating distance and light intensity ratio table information representing the relationship between an imaging distance and an optimal light intensity ratio.

Next, the control module 71 calculates the optimal light intensity ratio [LD1 ($\lambda_{445}$):LD2 ($\lambda_{405}$)] for the estimated imaging distance L. The distance and light intensity ratio table information, as shown in FIG. 6, is prepared in advance, which indicates the relationship between the imaging distance and the optimal light intensity ratio. The optimal light intensity ratio is set by referring to the distance and light intensity ratio table information. The distance and light intensity ratio table information is stored in the setting information storing module 79 so as to be referred by the control module 71 as needed. The control module 71 refers to the distance and light intensity ratio table information to set the emitted light intensity of the LD2 to be larger than the light intensity of the LD1 so that the imaging distance becomes shorter to emphasize the blood capillary of the superficial portion of the mucous membrane. As the imaging distance becomes longer, the emitted light intensity of the LD1 is set to be larger than the light intensity of the LD2 so as to be the illuminating light having high illumination intensity to ensure the brightness of the long distance view. Alternatively, in accordance with the imaging distance, the light intensity ratio for the short distance view in which the emitted light intensity of the LD2 is larger than the light intensity of the LD1 and the light intensity ratio for the long distance view in which the emitted light intensity of the LD1 is larger than the light intensity of the LD2 may be switched to control the light intensity ratio in two stages.

As described above, the control module 71 estimates the imaging distance from the observation image and turns ON/OFF the laser light sources LD1, LD2 with an optimal light intensity ratio in accordance with the estimated imaging distance, and therefore, the light intensity ratio is automatically changed so as to allow the operator to easily observe the subject.

Figure 7A:
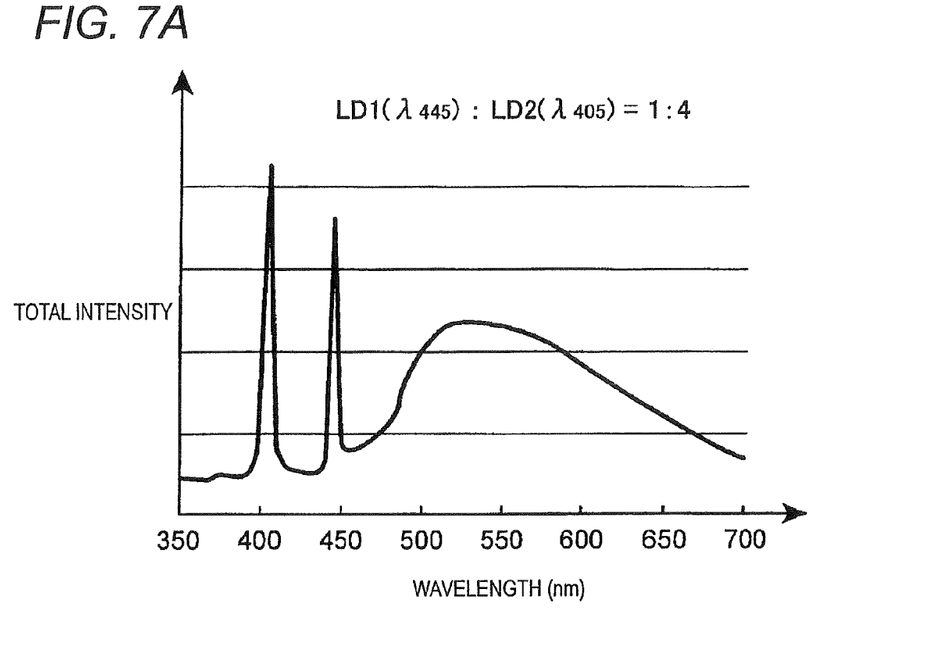
FIG. 7A is a graph illustrating a spectral intensity of the illuminating light when a light intensity ratio of LD1:LD2 is 1:4.
Figure 7B:
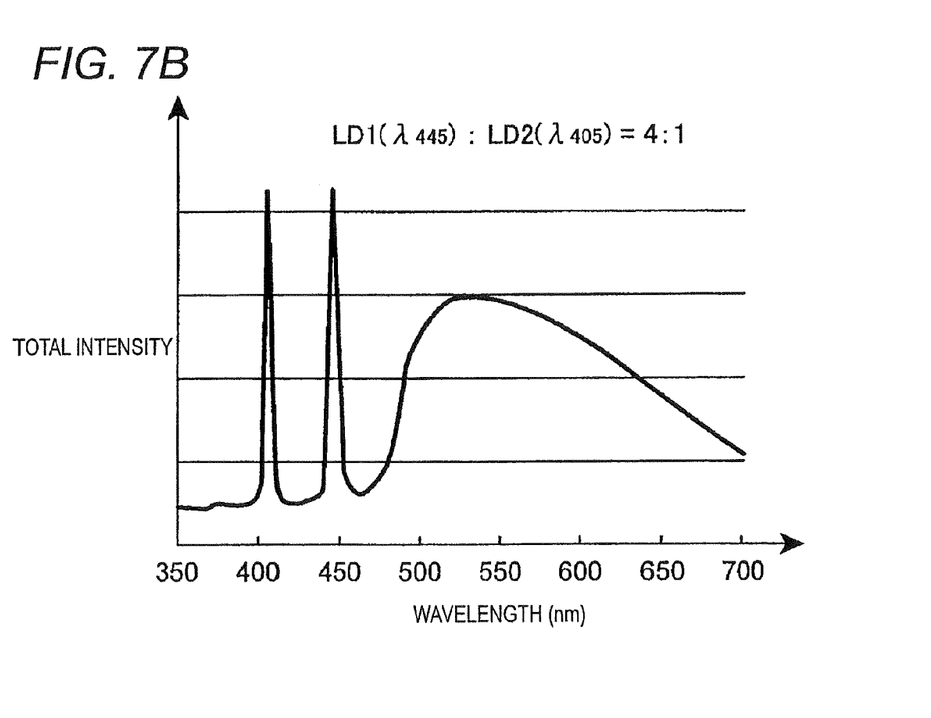
FIG. 7B is a graph illustrating a spectral intensity of the illuminating light when the light intensity ratio of LD1:LD2 is 4:1.

However, the emitted light of the laser light source LD1 is finally irradiated onto the subject as the white light and the emitted light of the laser light source LD2 is irradiated onto the subject as the violet light. Accordingly, if the light intensity ratio of the emitted light of the laser light sources LD1, LD2 is changed, the color tone of the illuminating light is changed. FIG. 7A is a graph illustrating a spectral intensity of illuminating light when a light intensity ratio of LD1:LD2 is 1:4, and FIG. 7B is a graph illustrating a spectral intensity of illuminating light when a light intensity ratio of LD1:LD2 is 4:1. If the light intensity of the LD2 is increased as compared with the light intensity of the LD1, the illuminating light becomes a bluish light and as a result, the color tone of the observation image is changed in accordance with the light intensity ratio.

Therefore, the color tone of the observation image is corrected in accordance with the color shade of the illuminating light that is changed by the set light intensity ratio (S6), so that the observation image is not affected by the change in the color shade of the illuminating light. The control module 71 outputs the information of the light intensity ratio set by the optimal light intensity ratio setting module 77 to the color tone correcting module 83 together with the image signal of the observation image. The color tone correcting table for every light intensity ratio is prepared in the setting information storing module 79, and the color tone correcting module 83 selectively refers to the color tone correcting table corresponding to the set light intensity ratio to correct the change in the color tone of the image (increase in the blue color) to be eliminated.

The color tone correcting table, for example, may be represented as a correcting matrix that corrects R, G, and B values using a matrix for each of the pixels of the observation image. If the correcting matrix is A, brightness values R', G', and B' of the pixels after correcting are represented by Equation (1).

$$(R'G'B') = A(RGB) = (a11\,a12\,a13\,a21\,a22\,a23\,a31\,a32\,a33)(RGB) \quad (1) \quad \#\#EQU00001\#\# \quad \text{Equation 1}$$

A coefficient a.sub.ij of the correcting matrix A is set to eliminate the change in the color shade of the illuminating light by the change in the light intensity ratio, so that a plurality kinds of correction matrixes A corresponding to the plurality kinds of light intensity ratios are prepared in advance. The information of the correcting matrixes is stored in the setting information storing module 79. The control module 71 uses the selected correcting matrix A to correct the RGB brightness values of each of the pixels of the observation image and outputs the corrected image to be obtained on the monitor 15.

The control module 71 continues the above procedures until the observation of the lesion area is completed (S7). Further, when another lesion area is found, the above procedures S4 to S6 are repeated. The procedures by the above sequence are performed until the observation is completed (S8).

As described above, even though the light intensity ratio of the illuminating light is changed by setting an optimal light intensity ratio, the color tone of the observation image is corrected in accordance with the set light intensity ratio. Therefore, even though any light intensity ratio is set, the image information may always be obtained as the observation image under constant color shade of the illuminating light. Accordingly, it is possible to always perform accurate endoscopic diagnosis. Further, various image processing that are subjected to the captured image, for example, a spectral endoscope image processing that creates a new observation image from the image intensity of a specific wavelength set (three primary colors), enhancement processing of various specific portions, or pseudo color processing is not affected by the change in the color shade of the illuminating light caused by changing the light intensity ratio of the laser light sources LD1, LD2.

Next, another example of endoscopic diagnosis by the above-mentioned endoscopic device will be described.

The endoscopic device with the present configuration, as shown in FIG. 1, newly includes a featured image region extracting module 81 that extracts a specific featured image region from the image signal.

Figures 8A, 8B:
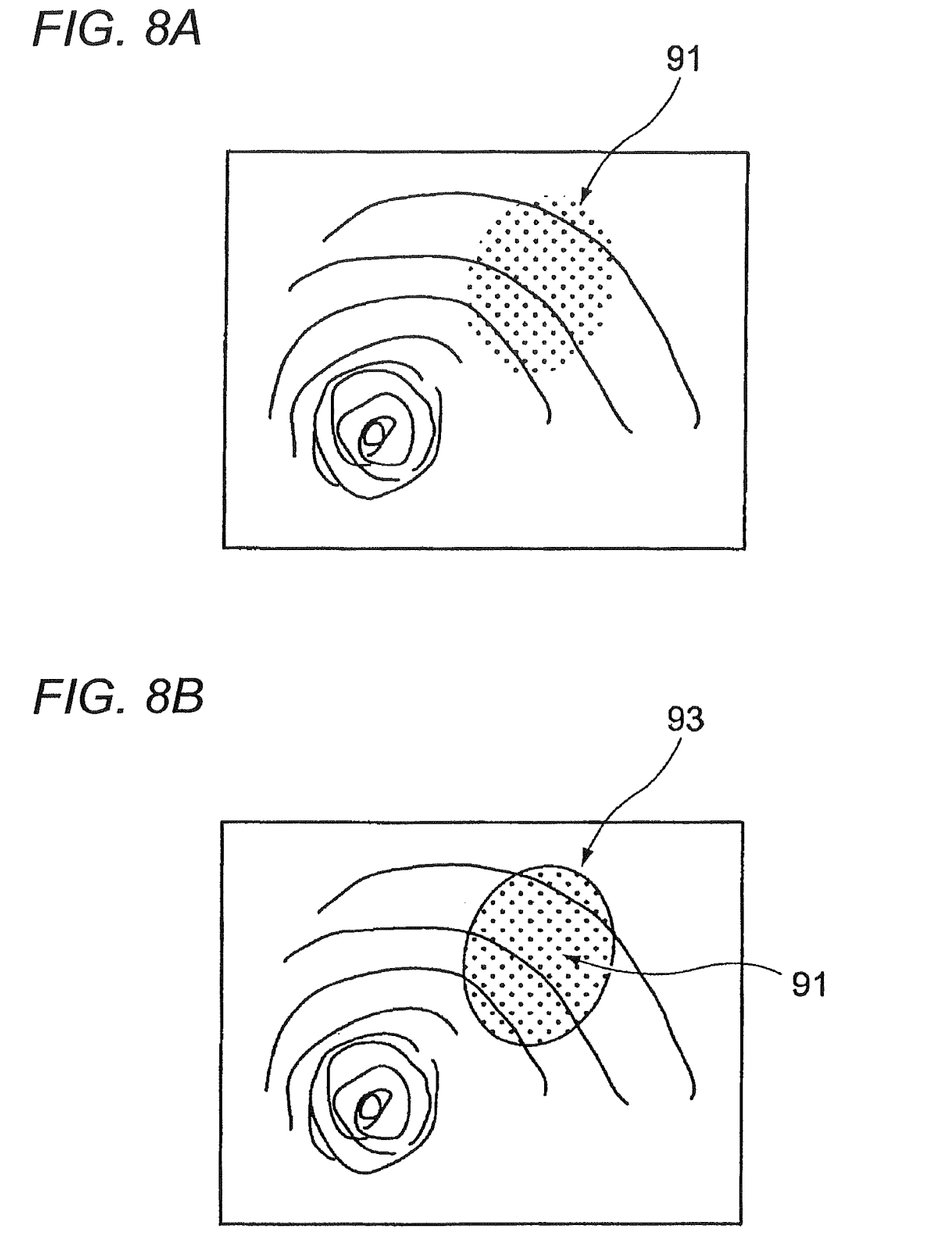
FIG. 8A is an explanatory diagram illustrating an observation image.
FIG. 8B is an explanatory diagram illustrating a state when a featured image region in the observation image is extracted.

FIG. 8A is an example of an observation image and shows an aspect that the blood capillary of a superficial portion of the mucous membrane in the image is displayed as a micro dot pattern. The dot pattern 91 that is the information of the blood capillary is brown as compared with the color of the surrounding pixels. Therefore, as shown in FIG. 8B, the featured image region 93 that is a blood capillary region may be selectively extracted by performing the image processing based on the color change information with respect to the surrounding pixels by the featured image region extracting module 81.

The control module 71 appropriately sets the light intensity ratio of the illuminating light so that the extracted featured image region 93 has a high S/N.

In order to provide an optimal light intensity ratio for the featured image region 93, the optimal light intensity ratio setting module 77 sets the optimal light intensity ratio by referring to the light intensity ratio for emphasizing the blood vessel stored in the setting information storing module 79 in advance. The light intensity ratio for emphasizing the blood vessel is a light intensity ratio in which that the intensity of the light emitted from the LD2 is set to be larger than the LD1 in order to emphasize the blood vessel of a superficial portion of the mucous membrane.

The control module 71 controls the light source control module 59 to have a set optimal light intensity ratio to emit desired illuminating light from the laser light sources LD1, LD2. With respect to the observation image output from the image pickup element 45, the color tone correcting module 83 selects a correcting matrix, as described above, to correct the RGB signal value using the selected correcting matrix.

As described, by irradiating the illuminating light with an optimal light intensity ratio for an area specified to the featured image region 93, an observation image that easily diagnoses the object to be observed is obtained. Further, the change in the color tone occurring in the observation image caused by the change in the light intensity ratio is corrected to obtain the same observation image as the illuminated by the illuminating light with the same color tone. Therefore, it is possible to increase the accuracy of the endoscopic diagnosis.

In the above exemplary embodiment, even though the featured image region 93 is extracted based on the color change in the observation image, especially, based on the information of a R signal value, a G signal value, and a B signal value, the featured image region including the blood capillary or micro pattern is simply extracted by calculating a ratio of the B signal value and the G signal value to which the blood vessel or the micro pattern of a superficial portion of the mucous membrane is emphasized to be displayed regardless of the information of the color signal. Further, other than the information of the color change or the change of the ratio of the B and G signals, for example, using a fact that the blood capillary is represented in the image as a micro pattern, the high frequency component may be extracted from the observation image to determine the featured image region 93. The high frequency component region, for example, is obtained by extracting a predetermined frequency component from a spectrum image, which is obtained by performing the two-dimensional Fourier transformation, using a mask processing and then performing inverse Fourier transformation on the extract result.

Next, a modified example that calculates the optimal light intensity ratio of the laser light sources LD1, LD2 from the information of the observation image without using the distance and light intensity ratio table information or the setting value such as the light intensity ratio for emphasizing the blood vessel, will be described.

If the light intensity ratio of the light emitted from the laser light sources LD1, LD2 is changed, the brightness contrast of the observation image is changed. Therefore, while measuring the light intensity ratio where the brightness contrast is at the maximum so as to be found, the light intensity ratio having the maximum brightness contrast is ultimately determined.

Figure 9A:
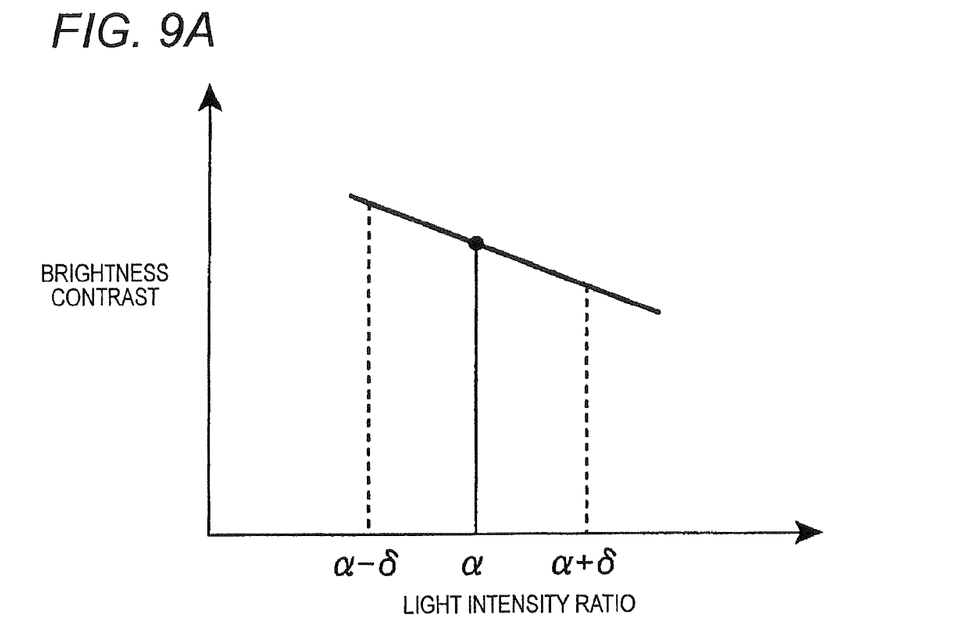
FIGS. 9A and 9B are explanatory diagrams illustrating specific procedures that calculate an optimal light intensity.
Figure 9B:
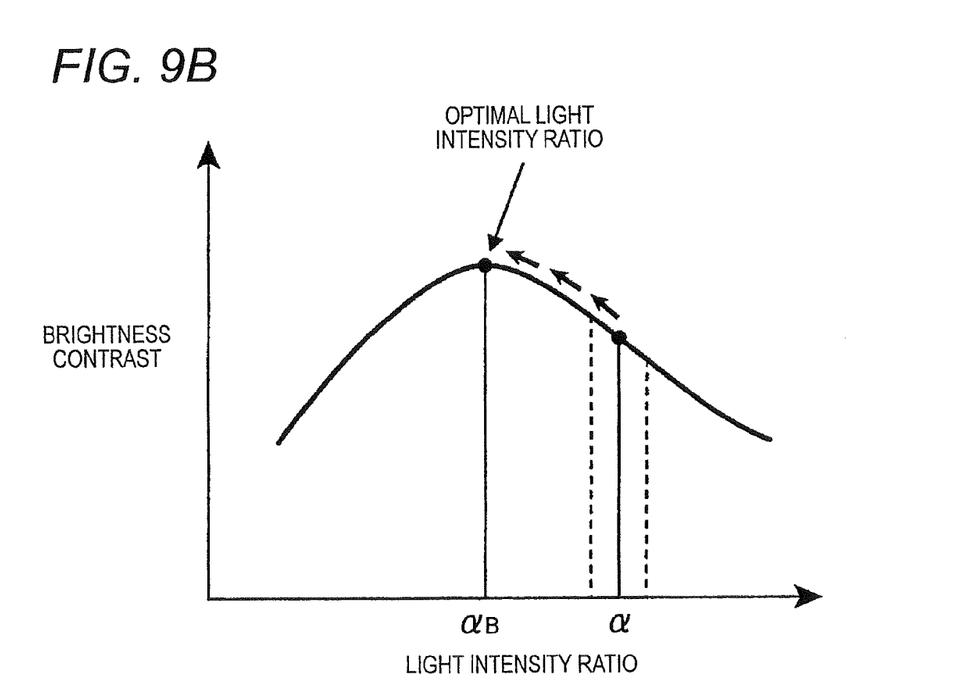

Explanatory diagrams illustrating specific procedures that calculate an optimal light intensity ratio are illustrated in FIGS. 9A and 9B. First, all of three kinds of light intensity ratios of an arbitrary light intensity ratio .alpha., a light intensity ratio .alpha.−.delta. in which a predetermined amount is subtracted from the arbitrary light intensity ratio .alpha., and a light intensity ratio .alpha.+.delta. in which the predetermined amount is added to the arbitrary light intensity ratio a are determined and the illuminating light is sequentially set with the light intensity ratios. In this case, the observation images by the illuminating light set with the light intensity ratios are captured to calculate the brightness contrast of three captured observation images.

As shown in FIG. 9A, when the brightness contrast is increased in a direction where the light intensity ratio is reduced from the light intensity ratio .alpha., the light intensity ratio is controlled to be reduced by the predetermined amount. In contrast, when the brightness contrast is increased in a direction where the light intensity ratio is increased from the light intensity ratio .alpha., the light intensity ratio is controlled to be increased by the predetermined amount. Further, with respect to the reduced or increased light intensity ratio, the above-mentioned procedures are repeated.

By doing this, as shown in FIG. 9B, since the light intensity ratio .alpha..sub.B in which the brightness contrast is the maximum is obtained, the light intensity ratio .alpha..sub.B is set as the optimal light intensity ratio. The control module 71 obtains the observation image irradiated with the set optimal light intensity ratio and outputs the information of the set optimal light intensity ratio to the color tone correcting module 83 together with the image signal of the observation image. The color tone correcting module 83, as described above, corrects the change in the color tone of the observation image to be eliminated by selectively referring to the color tone correction table corresponding to the set light intensity ratio.

As described above, the present invention is not limited to the above exemplary embodiments, but the combinations of the components of the exemplary embodiments or change or application based on the description of the specification or the known technology are also included in the present invention.

For example, even though laser light sources having different light emitting wavelength are used as a light source, the combination of a white light source such as a xenon lamp or a halogen lamp and a semiconductor light source such as a light emitting diode or a laser light source that emits a specific wavelength light, may be used.

As described above, the present specification discloses the following aspects.

(1) An endoscopic device that irradiates a plurality of illuminating light having different spectrums from each other onto a subject at a front edge of an endoscope inserting module and captures the subject to obtain an observation image, including:

an illuminating module configured to generate the plurality of illuminating light;

an imaging module configured to capture the subject and output an image signal of the observation image;

a light intensity ratio control module configured to control the illuminating module so as to irradiate the plurality of illuminating light onto the subject with a set light intensity ratio by setting the light intensity ratio of the plurality of illuminating light for every observation image; and a color tone correcting module configured to correct the color tone of the image signal so as to obtain the observation image with substantially the same color tone even though the light intensity ratio is changed.

According to the endoscopic device, when the illuminating light is emitted from the plurality of light sources that emit light having different spectrums, even though the light intensity ratio of the illuminating light is changed, the observation image may be corrected without changing the color tone of the observation image. Therefore, the subject may be observed with the illuminating light at an optimal light intensity ratio, and accurate endoscope diagnosis may be achieved.

(2) The endoscopic device of (1), wherein the light intensity ratio control module includes an imaging distance estimating module configured to estimate an imaging distance from the front edge of the endoscope inserting module to the subject and sets the light intensity ratio based on the imaging distance estimated by the imaging distance estimating module.

According to the endoscopic device, the light intensity ratio may be appropriately changed at the time of near view imaging having short imaging distance and at the time of distant view imaging having a long imaging distance. Therefore, for example, the near view imaging that is required to perform the narrow band imaging and the distant view imaging where the distance portion is tend to be dark are performed by the illuminating light at an optimal light intensity ratio so that the color tone of the observation image is not varied in accordance with the distance.

(3) The endoscopic device of (2), wherein the imaging distance estimating module calculates the imaging distance based on an AE value set in the imaging module and the entire light intensity of the plurality of illuminating light that is irradiated on the subject.

According to the endoscopic device, the imaging distance may be simply and precisely obtained from the information of the AE value and the information of the illuminating light intensity.

(4) The endoscopic device of any one of (1) to (3), wherein the color tone correcting module includes a correction information storing module in which correction information for correcting the color tone of the image signal corresponding to the light intensity ratio set by the light intensity ratio control module is stored in advance and corrects the color tone corresponding to the light intensity ratio by referring to the correction information of the correction information storing module.

According to the endoscopic device, the color tone correcting module corrects the color tone of the image signal using the correction information of the correction information storing module, to simply eliminate the change in the color tone of the observation image due to the set light intensity ratio.

(5) The endoscopic device of (4), wherein the correction information is a color tone correcting table that corrects R, G, and B values for pixels of the observation image using a matrix.

According to the endoscopic device, the color signal values of the observation image is corrected using matrix correction with high degree of freedom of a design so that various color tone adjustment may be easily applied.

(6) The endoscopic device of any one of (1) to (5), further comprising:

a featured image region extracting module configured to extract a featured image region included in the observation image from the image signal of the observation image, wherein the light intensity ratio control module sets the light intensity ratio so that the featured image region is suitable for the observation.

According to the endoscopic device, the featured image region may be observed by the illuminating light having an optimal light intensity ratio, and thus the change in the color tone of the observation image is not caused by the change in the light intensity ratio. Therefore, the featured image region may be precisely diagnosed.

(7) The endoscopic device of (6), wherein the featured image region has different color tone from the other region in the observation image.

According to the endoscopic device, an image region having different color from the surround pixel may be set as the featured image region.

(8) The endoscopic device of (7), wherein the featured image region is a blood capillary region of a superficial portion of the mucous membrane of the subject.

According to the endoscopic device, an image region which is turned in brown due to lots of the locally generated blood capillaries of a superficial portion of the mucous membrane may be set as the featured image region.

(9) The endoscopic device of (8), wherein the light intensity ratio control module sets the light intensity ratio by referring to the light intensity ratio for blood emphasis prepared in advance.

According to the endoscopic device, the blood capillary of a superficial portion of the mucous membrane may be observed with a standard degree of emphasis.

(10) The endoscopic device of (6), wherein the featured image region includes a high frequency component of a micro pattern of the superficial portion of the mucous membrane.

According to the endoscope device, for example, an image region having a high frequency component such as a region in which lots of the blood capillaries or micro patterns of a superficial portion of the mucous membrane locally appear is set as the featured image region.

(11) The endoscopic device of any one of (6) to (10), wherein the featured image region extracting module extracts the featured image region based on an R signal value, a G signal value, and a B signal value of the image signal.

According to the endoscopic device, the featured image region is extracted based on the respective color signal values of the captured image signal. Therefore, various extracting algorithm may be used, which gives lots of options for extract processing.

(12) The endoscopic device of any one of (6) to (10), wherein the featured image region extracting module extracts the featured image region based on a ratio of the B signal value and the G signal value of the image signal.

According to the endoscopic device, by calculating a ratio of the B signal value and the G signal value displayed by emphasizing the blood capillary or a micro pattern of a superficial portion of the mucous membrane, the location of the blood capillary or a micro pattern of the superficial portion of the mucous membrane is determined. Therefore, if the ratio of the B signal value and the G signal value is used, the featured image region may be simply extracted.

(13) The endoscopic device of any one of (6) to (10), wherein the featured image region extracting module obtains a high frequency component extracted image obtained by extracting a predetermined high frequency component by performing a mask processing onto the spectrum image obtained by performing the two-dimensional Fourier transformation on the image signal and performing an inverse Fourier transformation on the high frequency component extracted image to extract the featured image region including only the predetermined high frequency component.

According to the endoscopic device, the high frequency component may be precisely detected.

(14) The endoscopic device of any one of (1) to (13), wherein the plurality of illuminating light include a first illuminating light and a second illuminating light having a wavelength band narrower than the first illuminating light, and the illuminating module includes a first light source which is a light source of the first illuminating light, a second light source that is a light source of the second illuminating light, and a wavelength converting member that converts the wavelength of light emitted from the first light source to make the light as first illuminating light.

According to the endoscopic device, the first illuminating light having a broad spectrum is obtained and the color rendering properties is improved.

(15) The endoscopic device of (14), wherein the wavelength converting member is provided to simultaneously covert the wavelength of the light emitted from the first light source to use as the first illuminating light and convert the wavelength of the light emitted from the second light source to use as the second illuminating light, and the wavelength conversion efficiency of the wavelength converting member for the light emitted from the second light source is smaller than the wavelength conversion efficiency for the light emitted from the first light source.

According to the endoscopic device, the optical system is made simple and the light emitted from the second light source may be added without largely affecting the first illuminating light by the emitted light of the first light source.

(16) The endoscopic device of (14) or (15), wherein the first light source is a blue light emitting light source, the first illuminating light is white light, and the second light source emits light having a central wavelength in the range between 370 nm and 470 nm.

According to the endoscopic device, the subject is illuminated by visible light having a short wavelength from the second light source to obtain an observation image in which the blood capillary or the micro pattern of the superficial portion of the mucous membrane is emphasized, which increases the accuracy of the diagnosis.

The invention claimed is:

1. An endoscopic device that irradiates a plurality of illuminating lights having different spectrums from each other onto a subject at a front edge of an endoscope inserting module and captures the subject to obtain an observation image, comprising:

an illuminating module that generates the plurality of illuminating lights;

an imaging module that captures the subject and outputs an image signal of the observation image;

a light intensity ratio control module that controls the illuminating module to irradiate the plurality of illuminating lights onto the subject with a set light intensity ratio by setting the light intensity ratio of the plurality of illuminating lights for every observation image; and a color tone correcting module that corrects the color tone of the image signal so as to obtain the observation image with substantially a same color tone even though the light intensity ratio is changed, wherein the light intensity ratio control module obtains an image contrast of the observation image and changes the set light intensity ratio to a new light intensity ratio such that the image contrast becomes a maximum, wherein the light intensity ratio control module:
sets a first light intensity ratio, a second light intensity ratio in which an amount is subtracted from the first light intensity ratio, and a third light intensity ratio in which the amount is added to the first light intensity ratio;
sets the light intensity ratio of the illuminating light to the first, the second, and the third light intensity ratios, sequentially, to obtain respective observation images and image contrasts thereof; and
changes the new light intensity ratio by reducing the set light intensity ratio by a first amount when the image contrast is increased in a direction where the light intensity ratio is reduced from the first light intensity ratio, or changes the new light intensity ratio by increasing the light intensity ratio by a second amount when the image contrast is increased in a direction where the light intensity ratio is increased from the first light intensity ratio, and wherein the light intensity ratio control module changes the set light intensity ratio to the new light intensity ratio based on the obtained image contrast of the observation image such that the image contrast becomes the maximum.

2. The endoscopic device according to claim 1, wherein the color tone correcting module includes a correction information storing module in which correction information for correcting the color tone of the image signal corresponding to the new light intensity ratio set by the light intensity ratio control module is stored and corrects the color tone corresponding to the new light intensity ratio by referring to the correction information stored in the correction information storing module.

3. The endoscopic device according to claim 1 wherein the correction information comprises a color tone correcting table that corrects R, G, and B values for pixels of the observation image using a matrix.

4. The endoscopic device according to claim 1, further comprising:
a featured image region extracting module that extracts a featured image region included in the observation image from the image signal of the observation image,
wherein the light intensity ratio control module sets the new light intensity ratio so that the featured image region is suitable for an observation.

5. The endoscopic device according to claim 4, wherein the featured image region has a different color tone from other regions in the observation image.

6. The endoscopic device according to claim 4, wherein the featured image region comprises a blood capillary region of a superficial portion of a mucous membrane of the subject.

7. The endoscopic device according to claim 1, wherein the light intensity ratio control module sets the new light intensity ratio by referring to a light intensity ratio for blood emphasis prepared in advance.

8. The endoscopic device according to claim 6, wherein the featured image region includes a high frequency component which comprises a micro pattern of a superficial portion of a mucous membrane.

9. The endoscopic device according to claim 6, wherein the featured image region extracting module extracts the featured image region based on an R signal value, a G signal value, and a B signal value of the image signal.

10. The endoscopic device according to claim 6, wherein the featured image region extracting module extracts the featured image region based on a ratio of a B signal value and a G signal value of the image signal.

11. The endoscopic device according to claim 6, wherein the featured image region extracting module obtains a high frequency component extracted image obtained by extracting a predetermined high frequency component by performing a mask processing onto a spectrum image obtained by performing a two-dimensional Fourier transformation on the image signal and performing an inverse Fourier transformation on the high frequency component extracted image to extract the featured image region including only the predetermined high frequency component.

12. The endoscopic device according to claim 1, wherein the plurality of illuminating lights include a first illuminating light and a second illuminating light having a wavelength band narrower than the first illuminating light, and
the illuminating module includes a first light source which comprises a light source of the first illuminating light, a second light source that comprises a light source of the second illuminating light, and a wavelength converting member that converts a wavelength of light emitted from the first light source to make the light as first illuminating light.

13. The endoscopic device according to claim 12, wherein the wavelength converting member is provided to simultaneously covert the wavelength of the light emitted from the first light source to use as the first illuminating light and convert the wavelength of the light emitted from the second light source to use as the second illuminating light, and a wavelength conversion efficiency of the wavelength converting member for the light emitted from the second light source is smaller than a wavelength conversion efficiency for the light emitted from the first light source.

14. The endoscopic device according to claim 12, wherein the first light source comprises a blue light emitting light source, the first illuminating light comprises white light, and the second light source emits light having a central wavelength in a range between 370 nm and 470 nm.

15. The endoscopic device according to claim 13, wherein the first light source comprises a blue light emitting light source, the first illuminating light comprises white light, and the second light source emits light having a central wavelength in a range between 370 nm and 470 nm.

16. The endoscopic device according to claim 1, wherein the light intensity ratio control module finds the maximum image contrast based on an image contrast of a plurality of obtained observation images.

* * * * *